(12) United States Patent
Diefenbacher et al.

(10) Patent No.: US 7,511,056 B2
(45) Date of Patent: Mar. 31, 2009

(54) TGF-β INHIBITORS

(75) Inventors: Clive Gideon Diefenbacher, Greenwood, IN (US); Thomas Albert Engler, Indianapolis, IN (US); Hong-Yu Li, Zionsville, IN (US); Sushant Malhotra, Los Altos, CA (US); Jason Scott Sawyer, Indianapolis, IN (US); Yan Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 186 days.

(21) Appl. No.: 11/577,094

(22) PCT Filed: Nov. 2, 2005

(86) PCT No.: PCT/US2005/039554

§ 371 (c)(1),
(2), (4) Date: Apr. 12, 2007

(87) PCT Pub. No.: WO2006/052568

PCT Pub. Date: May 18, 2006

(65) Prior Publication Data

US 2008/0262004 A1    Oct. 23, 2008

Related U.S. Application Data

(60) Provisional application No. 60/626,545, filed on Nov. 10, 2004.

(51) Int. Cl.
  *A01N 43/42*    (2006.01)
  *A61K 31/44*    (2006.01)
  *C07D 491/02*   (2006.01)
  *C07D 498/02*   (2006.01)
  *C07D 401/00*   (2006.01)

(52) U.S. Cl. ............ 514/300; 514/338; 546/121; 546/276.7

(58) Field of Classification Search ............ 546/121, 546/276.7; 514/300, 338
  See application file for complete search history.

(56) References Cited

U.S. PATENT DOCUMENTS 7,405,299 B2 *  7/2008  Beight et al. ............ 544/353

FOREIGN PATENT DOCUMENTS

WO    WO 2004/050659    6/2004
WO    WO 2005/092894    10/2005

* cited by examiner

*Primary Examiner*—D. Margaret Seaman
*Assistant Examiner*—Niloofar Rahmani
(74) *Attorney, Agent, or Firm*—Danica Hostettler; Tina M. Tucker

(57) ABSTRACT

The present invention is directed to inhibitors of TGF-β of Formula I:

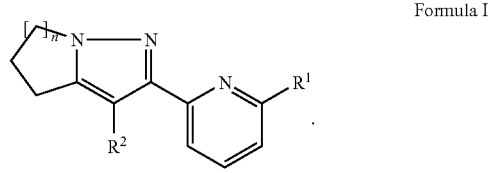

Formula I

4 Claims, No Drawings

TGF-β INHIBITORS

This is the national phase application, under 35 USC 371, PCT/US2005/039554, filed 2 Nov. 2005, which claims the benefit, under 35 USC 119(e), of U.S. provisional application 60/626,545 filed 10 Nov. 2004

FIELD OF THE INVENTION

The present invention relates to new compounds and their use as pharmaceutical agents, in particular their use as TGF-β signal transduction inhibitors.

BACKGROUND OF THE INVENTION

Transforming growth factor-beta (TGF-β) is a prototype for a large family of growth and differentiation factors that regulate development. TGF-β family members activate transmembrane serine/threonine receptor kinases, thereby initiating a signaling cascade via Smads, a novel class of intracellular signaling effectors that regulate gene expression. TGF-β is a potent inducer of growth arrest in many cell types, including epithelial cells. This activity is the basis of the tumor suppressor role of the TGF-β signaling system in carcinomas. Other activities, including TGF-β-induced epithelial-to-mesenchymal differentiation, contribute to cancer progression. TGF-β family signaling is of special relevance in mesenchymal differentiation, including bone development. Deregulated expression or activation of components of this signaling system can contribute to skeletal diseases, e.g. osteoarthritis. See Wakefield, et al. (2002) Current Opinion in Genetics & Development 12:22-29; Siegel, et al. (2003) Nature Reviews (Cancer) 3:807-820; Dumont, et al. (2003) Cancer Cell 3:531-536.

A number of compounds (for example WO 02/094833, WO 04/048382, WO 04/048381, WO 04/050659, WO 04/021989, WO 04/026871, WO 04/026307) have been identified as TGF-β inhibitors. However, there still remains a need for treatment in this field for compounds that are capable of inhibiting TGF-β signaling.

The present invention provides new inhibitors of TGF-β signaling useful for the treatment of conditions resulting from enhanced TGF-β activity or overproduction.

SUMMARY OF THE INVENTION

The present invention provides compounds of the formula:

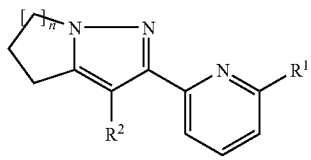

Formula I wherein
n is 1-2;
R¹ is hydrogen or $C_1$-$C_4$ alkyl;
R² is selected from the group consisting of 1-H-pyrrolo[2,3-b]pyridine, 1-H-pyrrolo[2,3-c]pyridine, 1-H-pyrazolo[3,4-b]pyridine, and 7-H-pyrrolo[2,3-d]pyrimidine all of which may be optionally substituted with $C_1$-$C_4$ alkyl or phenyl;
and the pharmaceutically acceptable salts thereof.

The present invention provides a pharmaceutical composition comprising compounds of Formula I and a pharmaceutically acceptable carrier, excipient, or diluent.

The present invention provides a method of inhibiting TGF-β in a mammal comprising administering to a mammal in need of such treatment an effective amount of a compound of Formula I.

The present invention further provides a method of treating conditions resulting from excessive TGF-β production in a mammal comprising administering to a mammal in need of such treatment a TGF-β-suppressing amount of a compound of Formula I.

In one of its method aspects, this invention is directed to a method for treating susceptible neoplasms comprising administering to a patient in need thereof an effective amount of a compound of Formula I.

In another of its method aspects, this invention is directed to a method for treating fibrosis comprising administering to a patient in need thereof an effective amount of a compound of Formula I.

The present invention provides compounds of Formula I for the manufacture of a medicament for the treatment of disorders associated with enhanced TGF-β activity or overproduction.

The present invention provides compounds of Formula I for use in therapy. The present invention provides for the use of compounds of Formula I for the manufacture of a medicament for the treatment of disorders associated with enhanced TGF-β activity or overproduction.

DETAILED DESCRIPTION OF THE INVENTION

The term "effective amount" as used in "an effective amount of a compound of Formula I," for example, refers to an amount of a compound of the present invention that is capable of inhibiting TGF-β signal transduction.

1-H-pyrrolo[2,3-b]pyridine means

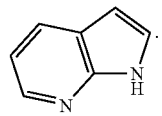

1-H-pyrrolo[2,3-c]pyridine means

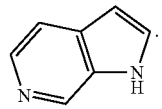

1-H-pyrazolo[3,4-b]pyridine means

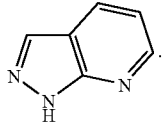

7-H-pyrrolo[2,3-d]pyrimidine means

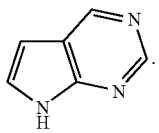

Abbreviations used herein include the following:
The term Pd$_2$(dba)$_3$ refers to tris(dibenzylideneacetone) dipalladium.
The term dppf refers to 1,1'-bis(diphenylphosphino) ferrocene.
The term DMAP=4-(N,N-dimethylamino)pyridine.
The term DMF refers to N,N-dimethylformamide.
The term DMSO refers to dimethylsulfoxide.
The term eq refers to equivalent.
The term ES refers to electron spray.
The term h refers to hour(s).
The term HPLC refers to high performance liquid chromatography.
The term L refers to liter.
The term min refers to minutes.
The term mL refers to milliliter.
The term mmol refers to millimole.
The term MPLC refers to medium pressure liquid chromatography.
The term MS refers to mass spectrum.
The term THF refers to tetrahydrofuran.
The term THP refers to tetrahydropyran.
The term TLC refers to thin layer chromatography.
The term TOF refers to time of flight.
The term W refers to watts.

The present invention contemplates specific classes of compounds of Formula I. The following paragraphs describe such specific classes:
(a) n is 1;
(b) R$^1$ is hydrogen;
(c) R$^1$ is methyl;
(d) R$^2$ is unsubstituted 1-H-pyrrolo[2,3-b]pyridine;
(e) R$^2$ is unsubstituted 1-H-pyrazolo[3,4-b]pyridine;
(f) R$^2$ is 1-H-pyrrolo[2,3-c]pyridine;
(g) R$^2$ is 7-H-pyrrolo[2,3-d]pyrimidine.

A number of diseases have been associated with TGF-β1 over production. Inhibitors of the TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post glaucoma drainage surgery are associated with TGF-β1 overproduction.

Fibrotic diseases associated with TGF-β1 overproduction can be divided into chronic conditions such as fibrosis of the kidney, lung and liver and more acute conditions such as dermal scarring and restenosis (Chamberlain, J. Cardiovascular Drug Reviews, 19(4):329-344). Synthesis and secretion of TGF-β1 by tumor cells can also lead to immune suppression such as seen in patients with aggressive brain or breast tumors (Arteaga, et al. (1993) J. Clin. Invest. 92:2569-2576). The course of Leishmanial infection in mice is drastically altered by TGF-β1 (Barral-Netto, et al. (1992) Science 257: 545-547). TGF-β1 exacerbated the disease, whereas TGF-β1 antibodies halted the progression of the disease in genetically susceptible mice. Genetically resistant mice became susceptible to Leishmanial infection upon administration of TGF-β1.

The profound effects of TGF-β1 on extracellular matrix deposition have been reviewed (Rocco and Ziyadeh (1991) in Contemporary Issues in Nephrology v.23, Hormones, autocoids and the kidney. ed. Jay Stein, Churchill Livingston, New York pp. 391-410; Roberts, et al. (1988) Rec. Prog. Hormone Res. 44:157-197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGF-β1 has profound effects on the kidney. The accumulation of mesangial matrix in proliferative glomerulonephritis (Border, et al. (1990) Kidney Int. 37:689-695) and diabetic nephropathy (Mauer, et al. (1984) J. Clin. Invest. 74:1143-1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90:1814-1818). TGF-β1 is an important mediator in the genesis of renal fibrosis in a number of animal models (Phan, et al. (1990) Kidney Int. 37:426; Okuda, et al. (1990) J. Clin. Invest. 86:453). Suppression of experimentally induced glomerulonephritis in rats has been demonstrated by antiserum against TGF-β1 (Border, et al. (1990) Nature 346:371) and by an extracellular matrix protein, decorin, which can bind TGF-β1 (Border, et al. (1992) Nature 360:361-363).

Too much TGF-β1 leads to dermal scar-tissue formation. Neutralizing TGF-β1 antibodies injected into the margins of healing wounds in rats have been shown to inhibit scarring without interfering with the rate of wound healing or the tensile strength of the wound (Shah, et al. (1992) Lancet 339:213-214). At the same time there was reduced angiogenesis, reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGF-β1 gene, TGF-β1 gene expression was associated with both extracellular matrix synthesis and hyperplasia (Nabel, et al. (1993) Proc. Natl. Acad.

Sci. USA 90:10759-10763). The TGF-β1 induced hyperplasia was not as extensive as that induced with PDGF-BB, but the extracellular matrix was more extensive with TGF-β1 transfectants. No extracellular matrix deposition was associated with FGF-1 (a secreted form of FGF) induced hyperplasia in this gene transfer pig model (Nabel (1993) Nature 362:844-846).

There are several types of cancer, i.e., susceptible neoplasms, where TGF-β1 produced by the tumor may be deleterious. MATLyLu rat prostate cancer cells (Steiner and Barrack (1992) Mol. Endocrinol. 6:15-25) and MCF-7 human breast cancer cells (Arteaga, et al. (1993) Cell Growth and Differ. 4:193-201) became more tumorigenic and metastatic after transfection with a vector expressing the mouse TGF-β1. TGF-1 has been associated with angiogenesis, metastasis and poor prognosis in human prostate and advanced gastric cancer (Wikstrom, P., et al. (1998) Prostate 37: 19-29; Saito, H. et al. (1999) Cancer 86: 1455-1462). In breast cancer, poor prognosis is associated with elevated TGF-β (Dickson, et al. (1987) Proc. Natl. Acad. Sci. USA 84:837-841; Kasid, et al. (1987) Cancer Res. 47:5733-5738; Daly, et al. (1990) J. Cell Biochem. 43:199-211; Barrett-Lee, et al. (1990) Br. J. Cancer 61:612-617; King, et al. (1989) J. Steroid Biochem. 34:133-138; Welch, et al. (1990) Proc. Natl. Acad. Sci. USA 87:7678-7682; Walker, et al. (1992) Eur. J. Cancer 238:641-644) and induction of TGF-β1 by tamoxifen treatment (Butta, et al. (1992) Cancer Res. 52:4261-4264) has been associated with failure of tamoxifen treatment for breast cancer (Thompson, et al. (1991) Br. J. Cancer 63:609-614). Anti TGF-β1 antibodies inhibit the growth of MDA-231 human breast cancer cells in athymic mice (Arteaga, et al. (1993) J. Clin. Invest. 92:2569-2576), a treatment which is correlated with an increase in spleen natural killer cell activity. CHO cells transfected with latent TGF-β1 also showed decreased NK activity and increased tumor growth in nude mice (Wallick, et al. (1990) J. Exp. Med. 172:1777-1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328:1592-1598). Patients with high circulating TGF-β before high dose chemotherapy and autologous bone marrow transplantation are at high risk for hepatic veno-occlusive disease (15-50% of all patients with a mortality rate up to 50%) and idiopathic interstitial pneumonitis (40-60% of all patients). The implication of these findings is 1) that elevated plasma levels of TGF-β1 can be used to identify at risk patients and 2) that reduction of TGF-β1 signaling could decrease the morbidity and mortality of these common treatments for breast cancer patients.

Many malignant cells secrete transforming growth factor-β (TGF-β), a potent immunosuppressant, suggesting that TGF-β production may represent a significant tumor escape mechanism from host immunosurveillance. Establishment of a leukocyte sub-population with disrupted TGF-β signaling in the tumor-bearing host offers a potential means for immunotherapy of cancer. A transgenic animal model with disrupted TGF-β signaling in T cells is capable of eradicating a normally lethal TGF-β over expressing lymphoma tumor, EL4 (Gorelik and Flavell, (2001) Nature Medicine 7(10): 1118-1122). Down regulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerized host. The immunosuppressive effects of TGF-β have also been implicated in a subpoptilation of HIV patients with lower than predicted immune response based on their CD4/CD8 T cell counts (Garba, et al. J. Immunology (2002) 168: 2247-2254). A TGF-β neutralizing antibody was capable of reversing the effect in culture, indicating that TGF-β signaling inhibitors may have utility in reversing the immune suppression present in this subset of HIV patients.

During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. The dual tumor suppression/tumor promotion roles of TGF-β have been most clearly elucidated in a transgenic system over expressing TGF-β in keratinocytes. While the transgenics were more resistant to formation of benign skin lesions, the rate of metastatic conversion in the transgenics was dramatically increased (Cui, et al (1996) Cell 86(4):531-42). The production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β on cell/cell and cell/stroma interactions result in a greater propensity for invasion and metastasis. Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities such as radiation therapy and chemotherapy induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β-mediated signal transduction might be a very effective therapeutic strategy. The resistance of tumor cells to TGF-β has been shown to negate much of the cytotoxic effects of radiation therapy and chemotherapy and the treatment-dependent activation of TGF-β in the stroma may even be detrimental as it can make the microenvironment more conducive to tumor progression and contributes to tissue damage leading to fibrosis. The development of a TGF-β signal transduction inhibitor is likely to benefit the treatment of progressed cancer alone and in combination with other therapies.

TGF-β inhibitors would also be useful against atherosclerosis (T. A. McCaffrey: TGF-βs and TGF-β Receptors in Atherosclerosis: Cytokine and Growth Factor Reviews 2000, 11, 103-114) and Alzheimer's (Masliah, E.; Ho, G.; Wyss-Coray, T.: Functional Role of TGF-β in Alzheimer's Disease Microvascular Injury: Lessons from Transgenic Mice: Neurochemistry International 2001, 39, 393-400) diseases.

The compounds disclosed herein can be made according to the following schemes and examples. The examples should in no way be understood to be limiting in any way as to how the compounds may be made.

The compounds of the present invention can be prepared by a variety of procedures, some of which are illustrated in the Schemes below. It will be recognized by one of skill in the art that the individual Steps in the following schemes may be varied to provide the compounds of Formula (I). The particular order of Steps required to produce the compounds of Formula (I) is dependent upon the particular compound being synthesized, the starting compound, and the relative liability of the substituted moieties. It will be understood that substituents such as $R^1$, $R^2$, n, etc. are as defined above unless otherwise specified and n is an integer from 1-2. R is H, $C_1$-$C_4$ alkyl, or cyclic boronate.

SCHEME I:

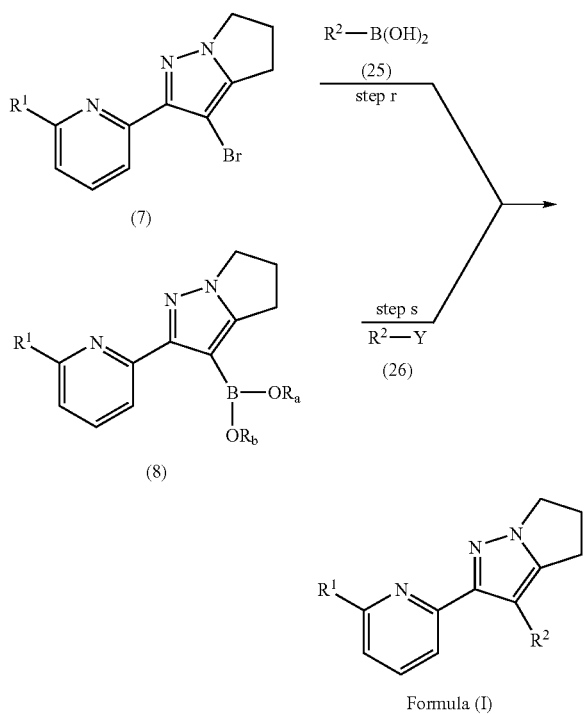

Scheme I, step r, depicts the palladium catalyzed coupling of a compound of formula (7) with a compound of formula (25) to give a compound of the invention (Formula I). Typically, the compound of formula (7) is reacted with a compound of formula (25) in the presence of a suitable catalyst, preferably tetrakis(triphenylphosphine) palladium(0), and a suitable base such as sodium carbonate, to give compounds of Formula (I) (Suzuki reaction see: Miryaura, N.; Yanagi, T.; Suzuki, A. The Palladium-Catalyzed Cross Coupling Reaction of Phenylboronic Acid with Haloarenes in the Presence of Bases. *Synth. Commun.*, 1981, 513-518). The compounds of formula (25) may be produced by methods known in the art (Li, Wenjie; Nelson, Dorian P. et al, *J. Org. Chem.*, 2002, 5394-5397). Similarly, a compound of formula (8) is reacted with a compound of formula (26), where Y can be an appropriate leaving group such as a halide, in the presence of a suitable palladium catalyst, preferably tetrakis(triphenylphosphine) palladium(0), and a suitable base such as potassium carbonate to provide further compounds of Formula (I) (Suzuki reaction see: Miryaura, N.; Yanagi, T.; Suzuki, A. The Palladium-Catalyzed Cross Coupling Reaction of Phenylboronic Acid with Haloarenes in the Presence of Bases. *Synth. Commun.*, 1981, 513-518). For examples (1) up to (8), $R_a = R_b = C_1$-$C_4$ alkyl; and for examples equal or greater than (8) $R_a = R_b = H$, $C_1$-$C_4$ alkyl, or $R_a$ and $R_b$ together form a 5-membered ring cycloboronate.

SCHEME II:

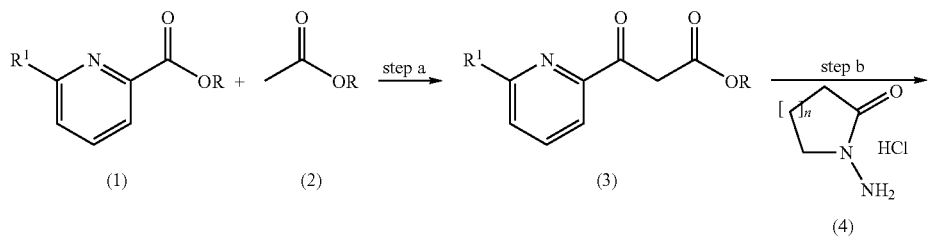

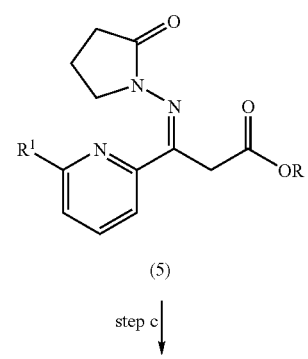

step c

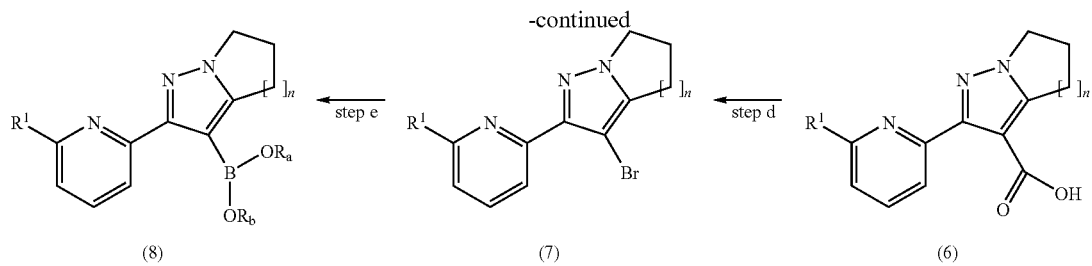

Scheme II, step a, depicts a condensation of two appropriately substituted esters, where OR for both compounds (1) and (2) is a $C_1$-$C_6$ alkoxy group. The products (3) can be isolated and purified by techniques well known in the art, such as precipitation, filtration, extraction, evaporation, trituration, chromatography, and recrystallization.

In Scheme II, step b, compound (3) is condensed with the appropriate hydrazine compound (4), to give the imine (5). Typically, the reaction is carried out in a suitable solvent such as ethanol, N-methylpyrrolidin-2-one, or preferably pyridine. The reaction is carried out at temperatures of about 60° C. to ambient for 4-24 hours. The products can be isolated and purified by techniques described above.

Step c depicts the cyclization of a compound (5) to give the fused heterocyclic acid (6). Typically, the appropriate compound (5) is reacted with a suitable base, preferably cesium carbonate in a suitable solvent preferably N,N-dimethylformamide (DMF) at temperatures of about 0 to 100° C. Optionally, a saponification of an intermediate carboxyl ester formed by cyclization c can be performed using lithium, sodium, or potassium hydroxide giving compound (6). The products can be isolated and purified by techniques described above.

Step d depicts the transformation of a carboxylic acid (6), to a halide (7). This transformation is well known and appreciated in the art (Larock, R. C., *Comprehensive Organic Transformations*, 2$^{nd}$ Ed., copyright 1999, John Wiley & Sons, pp 741-742).

Step e depicts the transformation of a heteroaryl halide (7), to a heteroaryl boronic acid or ester of formula (8). This transformation is well known and appreciated in the art (Li, Wenjie; Nelson, Dorian P. et al, *J. Org. Chem.*, 2002, 5394-5397).

SCHEME III:

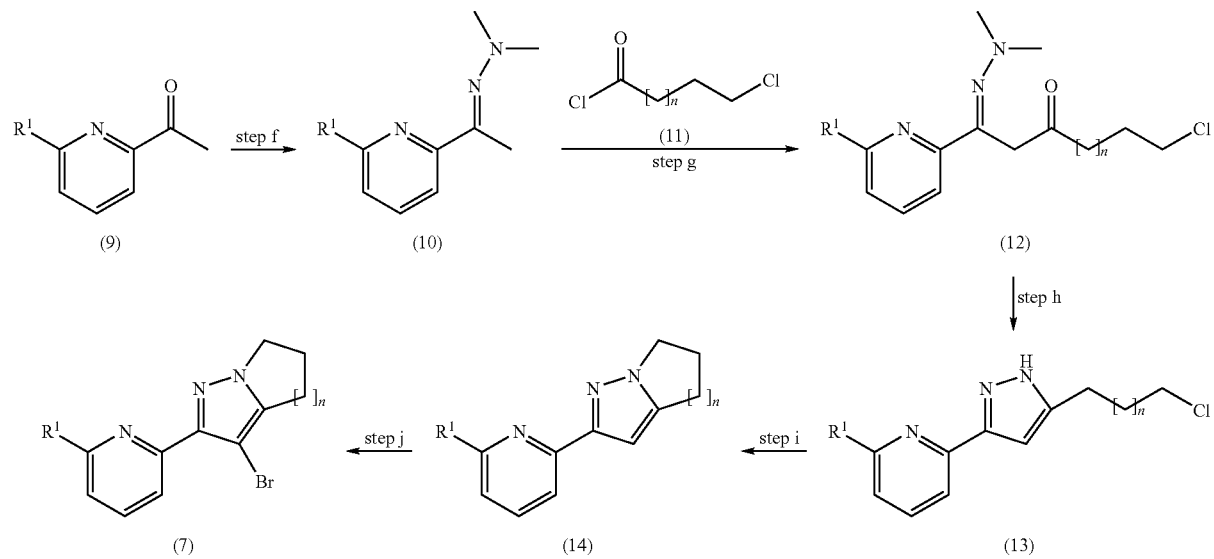

Scheme III depicts an alternative approach to the synthesis of the compound of formula (7). One skilled in the art would appreciate the conversion of various acetylpyridines of formula (9) to hydrazones of formula (10) through step f. This conversion is known in the art (*Org. Synth.* 1988, VI, pg 12, H. El Ouazzani, N. Khiar, I. Fernandez, and F. Alcudia, *J. Org. Chem.* 1997, 62, 287-291).

Scheme III, step g depicts the acylation of a hydrazone compound of formula (10) with a compound of formula (11) to give the product of formula (12). Typically the compound of formula (10) is contacted with a suitable base, such as potassium bis(trimethylsilyl)amide, lithium bis(trimethylsilyl)amide, sodium bis(trimethylsilyl)amide, sodium hydride, lithium hydride, potassium hydride, sodium alkoxides (sodium methoxide, or sodium ethoxide) or potassium alkoxides (potassium methoxide, or potassium ethoxide), or preferably lithium diisopropylamide. Generally, the reaction is carried out in suitable solvents, such as tetrahydrofuran (THF), toluene, or a combination of such, at temperatures of about −78°

C. to ambient temperature. The product, formula (12), can be isolated and purified by techniques well known in the art, such as precipitation, filtration, extraction, evaporation, trituration, chromatography, and recrystallization or can be carried forward in Scheme III without purification.

Scheme III, step h, depicts the conversion of a beta-ketohydrazone of formula (12) to a substituted pyrazole of formula (13). Typically, a compound of formula (12) is treated with a source of hydrazine such as hydrazine, hydrazine monohydrate, hydrazine hydrate, or preferably hydrazine hydrochloride in an appropriate solvent such as tetrahydrofuran, ethanol, methanol, water, or preferable a combination of these at temperatures of about ambient temperature to refluxing. The product, formula (13), can be isolated and purified by techniques well known in the art, such as precipitation, filtration, extraction, evaporation, trituration, chromatography, and recrystallization.

Scheme III, step i, depicts the cyclization of a haloalkylpyrazole compound of formula (13) to a 5,6-dihydro-4H-pyrrolo[1,2-b]pyrazole of formula (14). Typically, the appropriate compound of formula (13) is reacted with a suitable base, preferably sodium hydride in a suitable solvent, preferably N,N-dimethylformamide, at temperatures of about 0 to 100° C. The products of formula (14) can be isolated by methods described above.

Scheme III, step j, depicts the halogenation of a compound of formula (14) to give a compound of formula (7). Typically the appropriate compound of formula (14) is contacted with a halogenating agent such as N-bromosuccinimide in an appropriate solvent such as dichloromethane, chloroform, benzene, or preferably N,N-dimethylformamide, at temperatures of about 0 to 50° C.

The skilled artisan will also appreciate that not all of the substituents in the compounds of Formula (I) will tolerate certain reaction conditions employed to synthesize the compounds. These moieties may be introduced at a convenient point in the synthesis, or may be protected and then deprotected as necessary or desired. Furthermore, the skilled artisan will appreciate that in many circumstances, the order in which moieties are introduced is not critical.

The skilled artisan will also appreciate that the parent heterocycles defined in $R^2$ may be derivatized with benzenesulfonyl chloride and base, such as, triethylamine in a polar aprotic solvent, such as, methylene chloride.

The skilled artisan will appreciate that the compounds of Formula (I) may be formed into acid addition salts using pharmaceutically acceptable acids. The formation of acid-addition salts is well known and appreciated in the art.

The following preparations and examples further illustrate the preparation of compounds of the present invention and should not be interpreted in any way as to limit the scope. Those skilled in the art will recognize that various modifications may be made while not departing from the spirit and scope of the invention.

Preparation 1

2-[6-Methyl-(pyridin-2-yl)]-5,6-dihydro-4H-pyrrolo[1,2-b]pyrazole-3-boronic acid

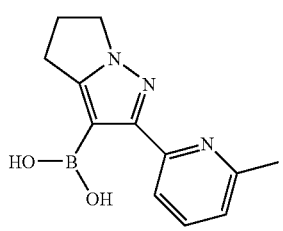

A. Preparation of 3-[6-Methyl-(pyridin-2-yl)]-3-oxo-propionic acid ethyl ester

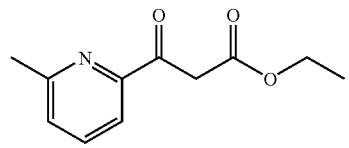

Stir a mixture of sodium ethoxide (90 g, 1.32 mol), toluene (0.5 L), and ethyl acetate (0.2 L, 1.98 mol) in a 2 L flask equipped with reflux condenser, mechanical stirrer, and nitrogen inlet. After 1 h, add 6-methyl-pyridine-2-carboxylic acid methyl ester (Cheung, Y, Tetrahedron Lett. 1979, 40, 3809-10; 100 g, 0.66 mol). Heat the mixture at reflux (92° C.) for 20 h. Cool the mixture to room temperature and acidify with glacial acetic acid to pH 6. Wash the resulting gel with water (0.5 L). Separate the layers and extract the aqueous layer with toluene (1×0.5 L). Dry the combined organic layers (sodium sulfate), filter, and concentrate in vacuo to yield the subtitled product (154 g) as a dark oil in 86% purity by HPLC analysis. MS (ES) m/z=208 (M+H).

B. Preparation of 3-[6-Methyl-(pyridin-2-yl)]-3-(2-oxo-pyrrolidin-1-ylimino)-propionic acid ethyl ester

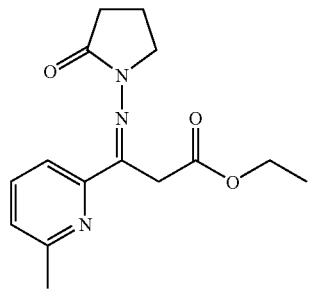

Add 1-aminopyrrolidin-2-one hydrochloride (Zubek, A. Z. Chem. 1969, 9(2), 58; 99.4 g, 0.73 mol) to a 3 L flask equipped with mechanical stirrer and nitrogen inlet. Add 3-[6-methyl-(pyridin-2-yl)]-3-oxo-propionic acid ethyl ester (Preparation 1, Part A; 154 g, 0.66 mol), and pyridine (280 mL). Stir the reaction mixture at room temperature for 20 h. Dilute the mixture with water (200 mL) and extract with toluene (2×250 mL). Combine the organic layers, filter, and concentrate in vacuo to yield the subtitled product (201 g) as a dark oil. MS (ES) m/z=290 (M+H).

C. Preparation of 2-[6-Methyl-(pyridin-2-yl)]-5,6-dihydro-4H-pyrrolo[1,2-b]pyrazole-3-carboxylic acid

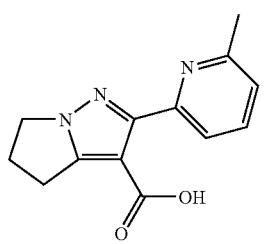

Add sodium ethoxide (90 g, 1.32 mol), toluene (5 L) and 3-[6-methyl-(pyridin-2-yl)]-3-(2-oxo-pyrrolidin-1-ylimino)-propionic acid ethyl ester (Preparation 1, Part B; 201 g, 0.661 mol) to a 22 L flask equipped with a mechanical stirrer, nitrogen inlet and a reflux condenser. Heat the mixture at 100° C. for 24 h then cool to room temperature. Add water (4 L) and adjust the pH to 4 with concentrated hydrochloric acid. Separate the organic layer and extract the aqueous portion with 10% isopropyl alcohol in chloroform (3×4.5 L). Combine the organic layers, dry (sodium sulfate), filter, and concentrate in vacuo to yield the subtitled product 138 g (86%) as a yellow solid in 78% purity by HPLC analysis. MS (ES) m/z=244 (M+H).

D. Preparation of 3-Bromo-2-[6-methyl-(pyridin-2-yl)]-5,6-dihydro-4H-pyrrolo[1,2b]pyrazole

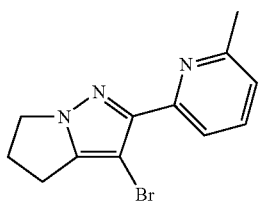

To a solution of 2-[6-methyl-(pyridin-2-yl)]-5,6-dihydro-4H-pyrrolo[1,2-b]pyrazole-3-carboxylic acid (Preparation 1, Part C; 1.4 g, 5.8 mmol) in N,N-dimethylformamide (20 mL) with N-bromosuccinamide (1 g, 5.6 mmol) and stir at room temperature for 16 h. Dilute the mixture with ethyl acetate and wash three times with water, once with aqueous sodium chloride, dry (sodium sulfate), filter, and concentrate in vacuo to yield 1.5 g (94%) of the title compound as light yellow solid. MS (ES) m/z=278 (M+H).

E. Preparation of 2-[6-Methyl-(pyridin-2-yl)]-5,6-dihydro-4H-pyrrolo[1,2-b]pyrazole-3-boronic acid Place tetrahydrofuran (28.0 mL) in a 100 mL round-bottom flask equipped with a temperature probe, a magnetic stirrer, and a septum and put under a nitrogen atmosphere. Add 3-bromo-2-[6-methyl-(pyridin-2-yl)]-5,6-dihydro-4H-pyrrolo[1,2-b]pyrazole (Preparation 1, Part D; 1.44 g, 5.18 mmol) and triisopropyl borate (3.10 mL, 13.5 mmol). Cool the mixture to −78° C. using a dry ice/acetone bath. Add 1.4M n-butyllithium in hexanes (8.80 mL, 12.4 mmol) dropwise via a syringe pump over 10 min keeping the temperature below −40° C. Remove the dry ice/acetone bath and allow the reaction mixture to warm to room temperature. Add saturated aqueous ammonium chloride (10 mL) and extract with chloroform (2×100 mL). Combine the organic layers, dry over anhydrous sodium sulfate, and remove the solvent under reduced pressure to afford an oil. Purify the oil by normal phase flash chromatography (120 g Biotage KP-Sil 40L: 100% ethyl acetate in hexanes for 25 min, 0-10% methanol in ethyl acetate in ramp over 15 min, then 10% methanol in ethyl acetate) to yield 910 mg (73%) of the title compound. MS (ES) m/z=244 (M+H).

Preparation 2

2-(Pyridin-2-yl)-5,6-dihydro-4H-pyrrolo[1,2-b]pyrazole-3-boronic acid

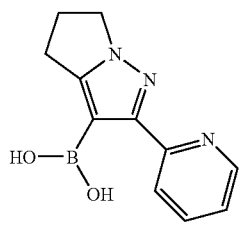

A. Preparation of 3-Oxo-3-(pyridin-2-yl)-propionic acid ethyl ester

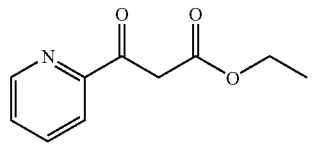

Stir a mixture of sodium ethoxide (360 g, 5.29 mol), toluene (4 L), ethanol (18 mL, 0.265 mol), and ethyl acetate (1.04 L, 10.6 mol) in a 22 L flask equipped with a reflux condenser, nitrogen inlet, and mechanical stirrer. Stir for 1 h as the mixture warms to 26° C. Add pyridine-2-carboxylic acid ethyl ester (Fluka; 400 g, 2.65 mol) and heat the mixture to reflux (90° C.) for 18 h. Cool the mixture to room temperature, dilute with toluene (8 L), wash with water (6 L), and separate the layers. Acidify the aqueous layer to pH 5 with glacial acetic acid. Extract with ethyl acetate (2×4 L), dry the combined organic layers (sodium sulfate), filter, and concentrate in vacuo to yield 466 g (91%) the subtitled compound as a dark oil in 93% purity by HPLC analysis. MS (ES) m/z=194 (M+H).

B. Preparation of 3-(2-Oxo-pyrrolidin-1-ylimino)-3-(pyridin-2-yl)-propionic acid ethyl ester

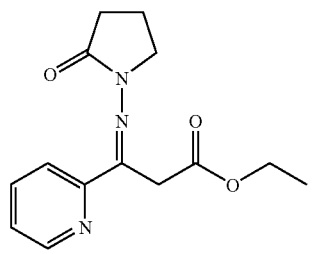

Place 1-aminopyrrolidin-2-one hydrochloride (Zubek, A. Z. Chem., 1969, 9(2), 58; 155.6 g, 1.14 mol) in a 3 L flask equipped with mechanical stirrer and nitrogen inlet. Add 3-oxo-3-pyridin-2-yl-propionic acid ethyl ester (Preparation 2, Part A; 200 g, 1.04 mol) and pyridine (400 mL). Stir the reaction mixture at room temperature for 20 h. Dilute the mixture with water (500 mL) and extract with toluene (2×500 mL). Combine the organic layers, dry (sodium sulfate), filter, and concentrate in vacuo to yield 280 g (98%) of the subtitled compound as a dark oil. MS (ES) m/z=276 (M+H).

C. Preparation of 2-(Pyridin-2-yl)-5,6-dihydro-4H-pyrrolo[1,2-b]pyrazole-3-carboxylic acid

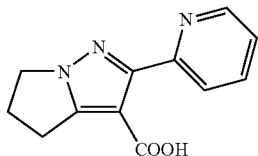

Add sodium ethoxide (145 g, 2.03 mol), followed by toluene (7 L) and 3-(2-oxo-pyrrolidin-1-ylimino)-3-(pyridin-2-yl)-propionic acid ethyl ester (Preparation 3, Part B; 280 g, 1.02 mol) to a 22 L flask equipped with mechanical stirrer, nitrogen inlet and a reflux condenser. Heat the mixture at 100° C. for 21 h. Cool to room temperature, add water (6 L), and adjust to pH 5 with concentrated hydrochloric acid. Separate the organic layer and extract the aqueous layer with 10% isopropyl alcohol in chloroform (2×9 L). Combine the organic layers, dry (sodium sulfate), filter, and concentrate in vacuo to yield 218 g (93%) of the title compound as a yellow solid MS (ES) m/z=230 (M+H).

D. Preparation of 3-Bromo-2-(pyridin-2-yl)-5,6-dihydro-4H-pyrrolo[1,2-b]pyrazole

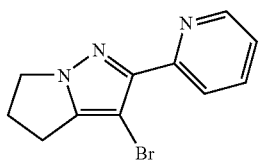

Stir a mixture of 2-(pyridin-2-yl)-5,6-dihydro-4H-pyrrolo[1,2-b]pyrazole-3-carboxylic acid (Preparation 2C; 2 g, 8.7 mmol), sodium bicarbonate (3.3 g, 38.4 mmol), and N-bromosuccinamide (1.7 g, 9.6 mmol) in DMF (50 mL) at room temperature for 2 h. Dilute the crude mixture with water (50 mL) and ethyl acetate (100 mL). Separate the ethyl acetate layer, extract with saturated sodium chloride solution, dry over anhydrous sodium sulfate, filter, and evaporate to a solid mass. Purify by MPLC (SiO$_2$, 1:1 ethyl acetate/hexane) to obtain 1.62 g (70%) of the title compound as a cream solid. MS (ES) m/z 264 (M+H).

E. Preparation of 2-(Pyridin-2-yl)-5,6-dihydro-4H-pyrrolo[1,2-b]pyrazole-3-boronic acid Place tetrahydrofuran (60.0 mL) in a 100 mL round-bottom flask equipped with a temperature probe, a magnetic stirrer, and a septum and put under a nitrogen atmosphere. Add 3-bromo-2-(pyridin-2-yl)-5,6-dihydro-4H-pyrrolo[1,2-b]pyrazole (Preparation 3, Part D; 3.00 g, 11.4 mmol) and triisopropyl borate (6.80 mL, 29.5 mmol). Cool the mixture to −78° C. using a dry ice/acetone bath. Add 1.41M n-butyllithium in hexanes (19.3 mL, 27.3 mmol) dropwise via a syringe pump over 10 min keeping the temperature below −40° C. Remove the dry ice/acetone bath and allow the reaction mixture to warm to room temperature. Add saturated aqueous ammonium chloride (20 mL) and extract with chloroform (2×150 mL). Combine the organic layers, dry over anhydrous sodium sulfate, and remove the solvent under reduced pressure to afford an oil. Purify by normal phase flash chromatography (120 g Biotage KP-Sil 40L: ethyl acetate for 25 min, 0-10% methanol in ethyl acetate in ramp over 15 min, then 10% methanol in ethyl acetate) to obtain 1.43 g (55%) of the title product. MS (ES) m/z=230 (M+H).

Preparation 3A

General Suzuki Coupling Method A

Add 2-(pyridin-2-yl)-5,6-dihydro-4H-pyrrolo[1,2-b]pyrazole-3-boronic acid (Preparation 2) or 2-[6-methyl-(pyridin-2-yl)]-5,6-dihydro-4H-pyrrolo[1,2-b]pyrazole-3-boronic acid (Preparation 1) (1.0 eq), the heteroaryl halide (1.0-1.2 eq.), sodium bicarbonate (2.0 eq.) or potassium carbonate (1.0 eq), tetrakis(triphenylphosphine) palladium (0) (Strem, 0.02-0.05 eq.), 50% aqueous dimethylsulfoxide (0.5 M), to a microwave reactor vessel. Seal the reactor vessel and irradiate with 50 watts of microwave radiation for 10 min at 110° C. Cool the reaction to room temperature. Dilute the reaction with methanol and load the mixture onto a Varian® Bond Elut™ SCX column. Rinse the column with absolute methanol, and then elute the column with 2 M ammonia in methanol. Purify by flash column chromatography (silica gel, eluting with the appropriate mixture of ethyl acetate/methanol) and concentrate in vacuo. If needed, further purify by recrystallization or reverse phase high-performance chromatography to provide the final compound.

Preparation 3B

General Suzuki Coupling Method B

Add 2-(pyridin-2-yl)-5,6-dihydro-4H-pyrrolo[1,2-b]pyrazole-3-boronic acid (Preparation 2) or 2-[6-methyl-(pyridin-2-yl)]-5,6-dihydro-4H-pyrrolo[1,2-b]pyrazole-3-boronic acid (Preparation 1)(1.0 eq) to the appropriate heteroaryl halide (1.2 equiv) in the presence of ([1,1']-bis(diphenylphosphino)ferrocene)dichloropalladium(II) (dppf Pd) (3-5% mol), a suitable ligand, preferably biphenyl-2-yl-di-tert-butyl-phosphane (6-10% mol), and a suitable base, preferably sodium carbonate (2.0 equiv-3.0 equiv) in dioxane, 4:1 dioxane/ethanol, or 1:1 DMSO/water in a 10 mL glass tube. Seal the reaction vessel with a septum and place in the microwave reactor. Use microwave irradiation to raise the temperature between 80-130° C. over 10-30 min. Alternatively, the tube is placed into a conventional oil bath and heated for 10-30 min at 110-140° C. Dilute the reaction mixture with chloroform/isopropyl alcohol and wash the solution with saturated sodium chloride solution. Dry the mixture solution over sodium sulfate and evaporate the solvents to give a viscous mixture. Purify the crude product via silica gel chromatography using dichloromethane-10:1 dichloromethane/methanol or dichloromethane-4:1 dichloromethane/tetrahydrofuran-10:1 dichloromethane/methanol as gradient-eluting solvents to give the desired compound.

Preparation 4

3-Boronic acid-2-aryl-5,6-dihydro-4H-pyrrolo[1,2-b]pyrazoles and 3-Boronic acid-2-aryl-4,5,6,7-tetrahydro-pyrazolo[1,5-a]pyridines

A. General Procedure for Preparation of 2-[5-(Alkylchloro)-1H-pyrazol-3-yl]-pyridines

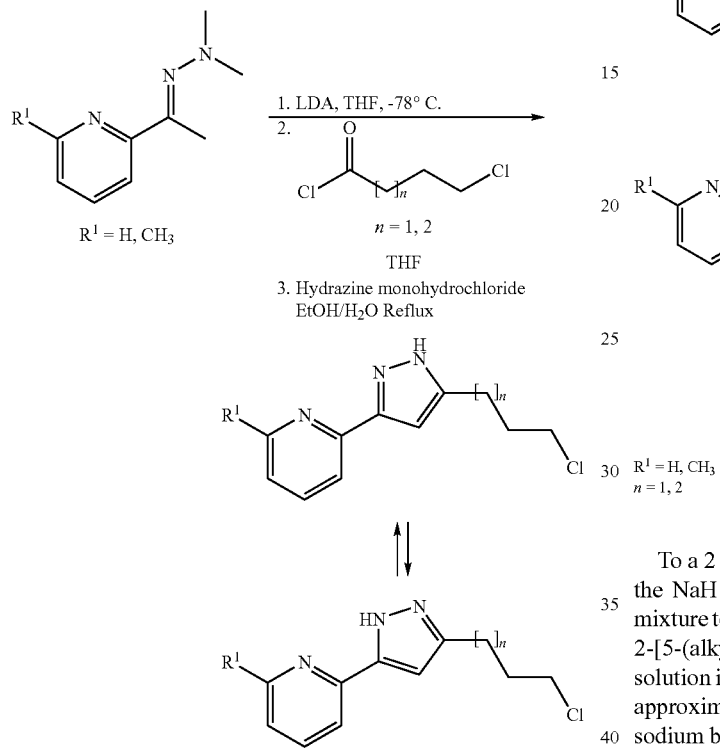

B. General Procedure for Preparation of 3-Bromo-2-aryl-5,6-dihydro-4H-pyrrolo[1,2-b]pyrazoles and 3-Bromo-2-aryl-4,5,6,7-tetrahydro-pyrazolo[1,5-a]pyridines

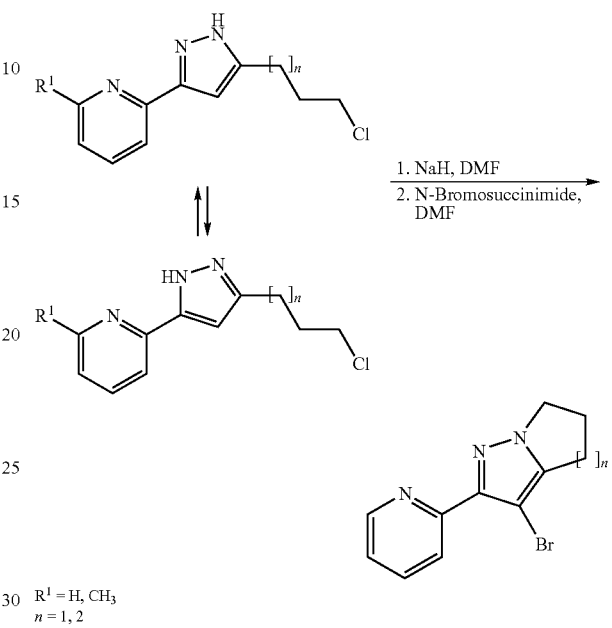

$R^1$ = H, $CH_3$
$n$ = 1, 2

Combine in a flask THF and diisopropylamine (1.3 eq) and cool to −78° C. and add 1.6M n-butyllithium in hexane (1.3 eq). Cool the solution of LDA to −78° C. and add the appropriate N,N-dimethylhydrazone (1 eq) drop-wise as a solution in THF via an addition funnel over ~30 min. Stir the resulting maroon-colored anion for ~30 min at −78° C. and cannulate into flask containing THF and the appropriate acid chloride (2.5 eq) at −78° C. Remove the cold bath upon completion of addition and allow the reaction mixture to warm to 0-5° C. Add hydrazine mono-hydrochloride (1.9 eq), 4:1 ethanol/water and heat at reflux for 2 h. Cool the reaction mixture and concentrate. Dilute with methylene chloride and water and transfer to a separatory funnel. Add saturated sodium bicarbonate, shake and separate layers. Extract the aqueous layer with methylene chloride, wash the combined organic layers with 1:1 saturated bicarbonate/brine and dry over sodium sulfate. Purify using a silica gel plug in a scintered glass funnel. Pre-wet the column with methylene chloride and pour the crude organic solution containing drying agent on top of the column. Elute with 75% hexane/25% ethyl acetate, 50% hexane/50% ethyl acetate, 25% hexane/75% ethyl acetate and concentrate to obtain the desired product in sufficient purity for use in the next step.

To a 2 L flask add NaH (60% oil dispersion, 1.2 eq). Wash the NaH with hexane three times and add DMF. Cool the mixture to 0° C. with an ice bath and introduce the appropriate 2-[5-(alkylchloro)-1H-pyrazol-3-yl]-pyridine (1 eq) as a solution in DMF over 30 min. Remove the ice bath and stir for approximately 1 h or until cyclization is complete. Introduce sodium bicarbonate (1.2 eq) and cool to 0° C. Add N-bromo-succinimide (1.1 eq) slowly and stir for ~15 min. Remove the cold bath, pour into water, extract into methylene chloride, wash the combined organic layers with water and brine, dry over sodium sulfate, filter, and concentrate. Purify using silica gel plug in a scintered glass funnel. Pre-wet the column with 75% hexane/ethyl acetate and pour the crude organic on top of the column using methylene chloride for the transfer. Elute with 75% hexane/25% ethyl acetate, 50% hexane/50% ethyl acetate, 25% hexane/75% ethyl acetate, and ethyl acetate step gradients to obtain the corresponding product.

C. General Procedure for Preparation of 3-Boronic acid-2-aryl-5,6-dihydro-4H-pyrrolo[1,2-b]pyrazoles and 3-Boronic acid-2-aryl-4,5,6,7-tetrahydro-pyrazolo[1,5-a]pyridines

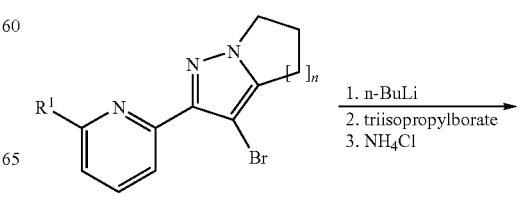

-continued

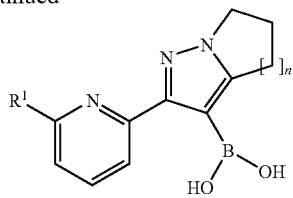

R¹ = H, CH₃
n = 1, 2

Cool a solution of the appropriate bromide (1 eq) in THF using a dry ice/diethyl ether bath to −74° C. Introduce 2.5 M n-butyllithium in hexanes (2 eq) at a rate such that the temperature does not exceed −60° C. and stir for 30 min. Add triisopropyl borate (4 eq) slowly and allow to warm to ~10° C. over 3 h. Dilute with saturated ammonium chloride solution and stir for 3 h to overnight. Concentrate and extract into methylene chloride. Collect white precipitate by filtration from the water layer and organic layer and rinse with water and dry. Concentrate the organic layer and triturate the residue with diethyl ether and/or hexane to give the corresponding product as a white solid. Combine solids for final isolation of the title compound(s).

Preparation 5

1-Benzene-sulfonyl-3-iodo-1H-pyrrolo[2,3-b]pyridine

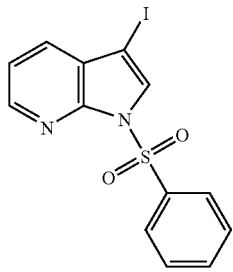

Add a solution of iodine monochloride (0.76 g, 4.7 mmol) in methylene chloride (4 mL) into a solution of 7-azaindole (Aldrich; 0.5 g, 4.2 mmol) in pyridine (4 mL) at 0° C. Stir the reaction at 0° C. for 15 min, then at room temperature for 30 min. Dilute with ethyl acetate and wash the organic phase with 1N aqueous hydrochloric acid (50 mL) and 1N aqueous sodium hydroxide (50 mL). Dry the organic layer (magnesium sulfate), filter, and concentrate in vacuo. Add DMAP (52 mg, 0.42 mmol), methylene chloride (14 mL), triethylamine (1.2 mL, 8.5 mmol), and benzenesulfonyl chloride (0.8 mL, 6.4 mmol) to the residue. Stir the mixture at room temperature for 18 h, then dilute with ethyl acetate. Wash the organic layer with 1N aqueous hydrochloric acid and saturated aqueous sodium bicarbonate. Dry the organic layer (sodium sulfate), filter, concentrate in vacuo, and purify by chromatography (silica gel, appropriate mixture of ethyl acetate and hexanes) to provide 1.0 g (64%) of the title compound as a tan solid. MS (ES) m/z=385 (M+H).

Preparation 6

5-Bromo-1H-pyrazolo[3,4-b]pyridine

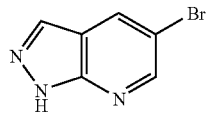

Dissolve 2-bromomalonaldehyde (Aldrich; 2.5 g, 16.5 mmol) and 3-aminopyrazole (Aldrich; 1.38 g, 16.5 mmol) in glacial acetic acid (25 mL) and reflux under nitrogen for 2 h. Concentrate under reduced pressure and dissolve the residue in absolute methanol (150 mL), vacuum filter through a pad of diatomaceous earth and concentrate under reduced pressure. Purify via chromatography (silica gel, hexane to 50% ethyl acetate/50% hexane) to obtain 365 mg (11%) of the title compound as a light yellow solid. TOF MS ES⁺ exact mass calculated for $C_6H_5N_3Br$ (p+H): m/z=197.9667, Found: 197.9674.

Preparation 7

5-Bromo-1-phenyl-1H-pyrazolo[3,4-b]pyridine

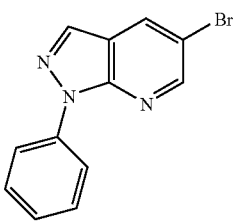

Dissolve 1-phenyl-5-aminopyrazole (Tokyo Kasei Kogyo Co. LTD; 1.5 g, 9.4 mmol) and 2-bromomalonaldehyde (Aldrich; 1.42 g, 9.4 mmol) in glacial acetic acid (170 mL) and reflux under nitrogen for 5 h. Concentrate under reduced pressure and purify via chromatography (silica gel, dichloromethane) to obtain 740 mg (28%) of the title compound as an off-white solid. TOF MS ES⁺ exact mass calculated for $C_{12}H_9N_3Br$ (p+H): m/z=273.9980, Found. 273.9965.

Preparation 8

1-Benzenesulfonyl-3-iodo-1H-pyrrolo[2,3-c]pyridine

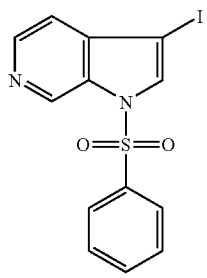

Utilize the same procedure as described for Preparation 5, except start with 6-azaindole (ref: Mahadevan, I.; Rasmussen, M.; *J. Heterocyclic Chem.*, 1992, 29, 359; 0.45 g, 3.8 mmol). Purify by silica gel chromatography, using the appropriate mixture of ethyl acetate and methylene chlororide, to provide 42% of the titled compound as a tan solid. MS (ES) m/z=385 (M+H).

Preparation 9

5-Bromo-1-methyl-1H-pyrazolo[3,4-b]pyridine

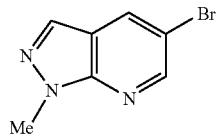

Dissolve 1-methyl-5-aminopyrazole (Butt Park LTD; 1.0 g, 10.3 mmol) and 2-bromomalonaldehyde (Aldrich; 1.55 g, 10.3 mmol) in glacial acetic acid (160 mL) and reflux under nitrogen for 48 h. Concentrate under reduced pressure and purify via chromatography (silica gel, 90% dichloromethane/10% diethyl ether) to obtain 610 mg (27%) of the title compound as an off-white solid. TOF MS ES⁺ exact mass calculated for $C_7H_7N_3Br$ (p+H): m/z=211.9823, Found: 211.9838.

Using the Suzuki coupling procedure as described in Preparation 3A, the following final product is obtained:

| Ex | Name | Product | Starting Material A | Starting Material B | Physical Data | Conditions |
|---|---|---|---|---|---|---|
| 1 | 4-[2-(Pyridin-2-yl)-5,6-dihydro-4H-pyrrolo[1,2-b]pyrazol-3-yl]-1H-pyrrolo[2,3-b]pyridine | 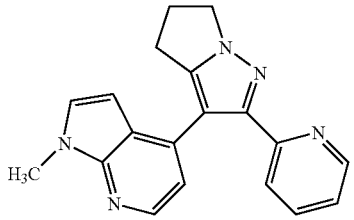 | 1-(4-Iodo-pyrrolo[2,3-b]pyridin-1-yl)-ethanone, Marcello Allegretti, et al., Synlett. 2001, 5, 609-612 | Prep 2 | TOF MS (ES) exact mass calc'd for $C_{18}H_{16}N_5$ (p + H): m/z = 302.1406, Found: 302.1397. | Prep 3A $K_2CO_3$, Re-crystallized. (yield = 37%) |

EXAMPLE 2

1-Methyl-4-[2-(pyridin-2-yl)-5,6-dihydro-4H-pyrrolo[1,2-b]pyrazol-3-yl]-1H-pyrrolo[2,3-b]pyridine

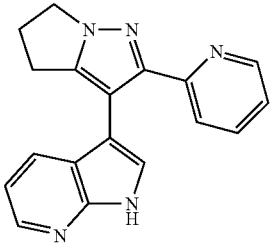

Dissolve 4-[2-(pyridin-2-yl)-5,6-dihydro-4H-pyrrolo[1,2-b]pyrazol-3-yl]-1H-pyrrolo[2,3-b]pyridine (Example 1; 0.150 g, 0.50 mmol) in N,N-dimethylformamide (10 ml). Add n-hexane (2 mL) and cool to 0° C. Add potassium hydride (35% suspension in mineral oil, 0.12 g, 1.0 mmol) and stir under nitrogen at 0° C. for 5 min. Add iodomethane (0.18 g, 1.3 mmol) and stir at 0° C. for 15 min. Dilute the reaction mixture by adding 1.0M aqueous hydrochloric acid (10 mL) and with excess diethyl ether. Extract the mixture with 0.2M aqueous hydrochloric acid. Combine the acidic aqueous extracts, add 5M aqueous sodium hydroxide until basic, and extract with dichloromethane. Concentrate the organic extracts under reduced pressure and purify via chromatography (silica gel, 95% ethyl acetate/5% methanol containing 0.1M ammonia) to obtain 0.125 g (79%) of the title compound as a cream colored solid. TOF MS (ES) exact mass calculated for $C_{19}H_{18}N_5$ (p+H): m/z=316.1562, Found: 316.1536.

EXAMPLE 3

3-[2-(Pyridin-2-yl)-5,6-dihydro-4H-pyrrolo[1,2-b]pyrazol-3-yl]-1H-pyrrolo[2,3-b]pyridine A. Preparation of 1-Benzenesulfonyl-3-(2-pyridin-2-yl-5,6-dihydro-4H-pyrrolo[1,2-b]pyrazol-3-yl)-1H-pyrrolo[2,3-b]pyridine

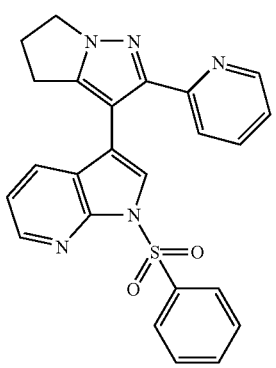

Using Preparation 3A, 1-benzene-sulfonyl-3-iodo-1H-pyrrolo[2,3-b]pyridine (Preparation 5) is reacted with 2-(pyridin-2-yl)-5,6-dihydro-4H-pyrrolo[1,2-b]pyrazole-3-boronic acid (Preparation 2) to provide the titled product. MS (ES) m/z=442 (M+H).

B. Preparation of 3-[2-(Pyridin-2-yl)-5,6-dihydro-4H-pyrrolo[1,2-b]pyrazol-3-yl]-1H-pyrrolo[2,3-b]pyridine Add potassium carbonate (21 mg, 0.15 mmol) to a solution of 1-benzenesulfonyl-3-[2-(pyridin-2-yl)-5,6-dihydro-4H-pyrrolo[1,2-b]pyrazol-3-yl]-1H-pyrrolo[2,3-b]pyridine (Example 3, Part A; 34 mg, 0.77 mmol) in methanol/water (0.9 mL/0.3 mL). Reflux the reaction overnight (16 h). Concentrate in vacuo, add aqueous sodium chloride (10 mL), and extract with chloroform (3×25 mL). Dry the combined organic extracts with sodium sulfate, filter, and concentrate in vacuo. Purify by flash column chromatography, using the appropriate mixture of methylene chloride, chloroform, methanol, and concentrated aqueous ammonium hydroxide, to provide 16 mg (68%) of the title compound as an off-white solid. MS (ES) m/z=302 (M+H).

Using the Suzuki coupling procedures as described in Preparation 3, the following final products are obtained:

| Ex | Name | Product | Starting Material A | Starting Material B | Physical Data | Conditions |
|---|---|---|---|---|---|---|
| 4 | 5-[2-[6-Methyl-(pyridin-2-yl)]-5,6-dihydro-4H-pyrrolo[1,2-b]pyrazol-3-yl]-1H-pyrazolo[3,4-b]pyridine | | Prep 6 | Prep 1 | TOF MS (ES) exact mass calc'd for $C_{18}H_{17}N_6$ (p + H): m/z = 317.1515, Found: 317.1518. | Prep 3A, $NaHCO_3$ Silica chromatography (EtOAc/MeOH) (yield = 56%) |
| 5 | 5-[2-(Pyridin-2-yl)-5,6-dihydro-4H-pyrrolo[1,2-b]pyrazol-3-yl]-1H-pyrazolo[3,4-b]pyridine | | Prep 6 | Prep 2 | TOF MS (ES) exact mass calc'd for $C_{17}H_{15}N_6$ (p + H): m/z = 303.1358, Found: 303.1373. | Prep 3A $K_2CO_3$, Recrystallized. (yield = 26%) |
| 6 | 4-[2-(Pyridin-2-yl)-5,6-dihydro-4H-pyrrolo[1,2-b]pyrazol-3-yl]-7H-pyrrolo[2,3-d]pyrimidine | | 4-Chloro-7H-pyrrolo-[2,3-d]-pyrimidine (Toronto) | Prep 2 | MS (ES) m/z = 303 (M + H) | Prep 3B |
| 7 | 4-[2-[6-Methyl-(pyridin-2-yl)]-5,6-dihydro-4H-pyrrolo[1,2-b]pyrazol-3-yl]-7H-pyrrolo[2,3-d]pyrimidine | | 4-Chloro-7H-pyrrolo-[2,3-d]-pyrimidine (Toronto) | Prep 1 | MS (ES) m/z = 317 (M + H) | Prep 3B |

-continued

| Ex | Name | Product | Starting Material A | Starting Material B | Physical Data | Conditions |
|---|---|---|---|---|---|---|
| 8 | 1-Methyl-5-[2-[6-methyl-(pyridin-2-yl)]-5,6-dihydro-4H-pyrrolo[1,2-b]pyrazol-3-yl]-1H-pyrazolo[3,4-b]pyridine | | Prep 9 | Prep 1 | TOF MS (ES) exact mass calc'd for $C_{19}H_{19}N_6$ (p + H): m/z = 331.1671, Found: 331.1655. | Prep 3A, NaHCO$_3$ Silica chromatography (EtOAc/ MeOH) (yield = 80%) |
| 9 | 1-Methyl-5-[2-(pyridin-2-yl)-4,5,6,7-tetrahydro-pyrazolo[1,5-a]pyridin-3-yl]-1H-pyrazolo[3,4-b]pyridine | | Prep 9 | 2-Pyridin-2-yl-4,5,6,7-tetra-hydro-pyrazolo-[1,5-a]pyridine-3-boronic acid (Prep 4) | TOF MS (ES) exact mass calc'd for $C_{19}H_{19}N_6$ (p + H): m/z = 331.1671, Found: 331.1659. | Prep 3A, NaHCO$_3$ Silica chromatography (EtOAc/ MeOH) (yield = 44%) |
| 10 | 1-Phenyl-5-[2-(pyridin-2-yl)-5,6-dihydro-4H-pyrrolo[1,2-b]pyrazol-3-yl]-1H-pyrazolo[3,4-b]pyridine | | Prep 7 | Prep 2 | TOF MS (ES) exact mass calc'd for $C_{23}H_{19}N_6$ (p + H): m/z = 379.1671, Found: 371.1674. | Prep 3A, NaHCO$_3$ Silica chromatography (EtOAc) Re-crystallized (yield = 60%) |
| 11 | 1-Methyl-5-[2-(pyridin-2-yl)-5,6-dihydro-4H-pyrrolo[1,2-b]pyrazol-3-yl]-1H-pyrazolo[3,4-b]pyridine | | Prep 9 | Prep 2 | TOF MS (ES) exact mass calc'd for $C_{18}H_{17}N_6$ (p + H): m/z = 317.1515, Found: 317.1515. | Prep 3A, NaHCO$_3$ Silica chromatography (EtOAc) (yield = 59%) |

EXAMPLE 12

3-[2-(Pyridin-2-yl)-5,6-dihydro-4H-pyrrolo[1,2-b]pyrazol-3-yl]-1H-pyrrolo[2,3-c]pyridine

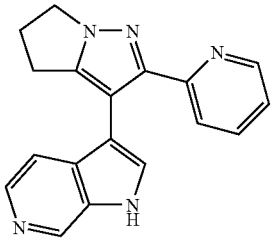

A. Preparation of 1-Benzenesulfonyl-3-(2-pyridin-2-yl-5,6-dihydro-4H-pyrrolo[1,2-b]pyrazol-3-yl)-1H-pyrrolo[2,3-c]pyridine

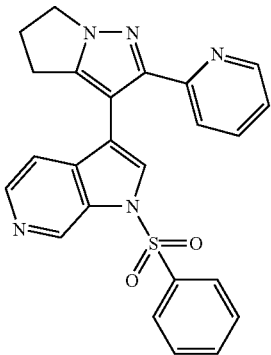

Using Preparation 3A, 1-benzenesulfonyl-3-iodo-1H-pyrrolo[2,3-c]pyridine (Preparation 8) is reacted with 2-(pyridin-2-yl)-5,6-dihydro-4H-pyrrolo[1,2-b]pyrazole-3-boronic acid (Preparation 2) to provide the titled product. MS (ES) m/z=442 (M+H).

B. Preparation of 3-[2-(Pyridin-2-yl)-5,6-dihydro-4H-pyrrolo[1,2-b]pyrazol-3-yl]-1H-pyrrolo[2,3-c]pyridine Add potassium carbonate (40 mg, 0.29 mmol) to a solution of 1-benzenesulfonyl-3-[2-(pyridin-2-yl)-5,6-dihydro-4H-pyrrolo[1,2-b]pyrazol-3-yl]-1H-pyrrolo[2,3-c]pyridine (Example 12, Part A; 16 mg, 0.036 mmol) in methanol (3 mL). Reflux the reaction mixture overnight (15 h). Concentrate the mixture in vacuo and purify by silica gel chromatography, using the appropriate mixture of methylene chloride, chloroform, methanol, and concentrated aqueous ammonium hydroxide, to provide 7 mg (64%) of the title compound as a tan solid. MS (ES) m/z=302 (M+H).

The compounds disclosed herein were tested by the following protocols for TGF-β inhibition, as described below in the protocol description.

TGF-β Receptor I Purification and In Vitro Kinase Reactions

For TGF-β Type I (RIT204D) Receptors:

The 6x-HIS tagged cytoplasmic kinase domain of each receptor was expressed and purified from Sf9 insect cell lysates as briefly described below:

Cell pellets after 48-72 h of infection were lysed in lysis buffer (LB: 50 mM Tris pH 7.5, 150 mM NaCl, 50 mM NaF, 0.5% NP40 with freshly added 20 mM β-mercaptoethanol, 10 mM imidazole, 1 mM PMSF, 1×EDTA-free Complete Protease Inhibitor (Boehringer Mannheim). Cell lysates were clarified by centrifugation and 0.45 uM filtered prior to purification by Ni/NTA affinity chromatography (Qiagen).

Chromatography Protocol:

Equilibrate with 10 CV of LB, load sample, wash with 10 CV RIPA buffer (50 mM Tris pH 7.5, 150 mM NaCl, 1% NP40, 1 mM EDTA, 0.25% sodium deoxycholate, added fresh 20 mM β-mercaptoethanol, 1 mM PMSF), wash with 10 CV LB, wash with 10 CV 1×KB (50 mM Tris pH 7.5, 150 mM NaCl, 4 mM $MgCl_2$, 1 mM NaF, 2 mM βmercaptoethanol), elute with a linear gradient of 1×KB containing 200 mM Imidazole. Both enzymes were approximately 90% pure and had autophosphorylation activity. Reactions: 170-200 nM enzyme in 1×KB, compound dilution series in 1×KB/16% DMSO (20 µM to 1 nM final concentration with 4% DMSO final concentration), reactions started by adding ATP mix (4 uM ATP/1 uCi $^{33}$P-γ-ATP final concentrations) in 1×KB.

Reactions were incubated at 30° C. for 1 h. Reactions were stopped and quantitated using standard TCA/BSA precipitation onto Millipore FB glass fiber filter plates and by liquid scintillation counting on a MicroBeta JET.

All the compounds exemplified herein inhibit the TGF-β Type I (RIT204D) receptor kinase domain with $IC_{50}$ values <1 µM.

Conditions "characterized by enhanced TGF-β activity" include those wherein TGF-β synthesis is stimulated so that TGF-β is present at increased levels or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, in either case "enhanced activity" refers to any condition wherein the biological activity of TGF-β is undesirably high, regardless of the cause.

The compositions of the present invention are therapeutically effective amounts of the TGF-β antagonists, noted above. The composition may be formulated with common excipients, diluents or carriers, and compressed into tablets, or formulated elixirs or solutions for convenient oral administration or administered by intramuscular intravenous routes. The compounds can be administered transdermally and maybe formulated as sustained release dosage forms and the like.

The method of treating a human patient according to the present invention includes administration of the TGF-β antagonists. The TGF-β antagonists are formulated into formulations which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations useful for separate administration of the TGF-β antagonists will normally consist of at least one compound selected from the compounds specified herein mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, for injection, and for oral ingestion.

We claim:
1. A compound of Formula I:

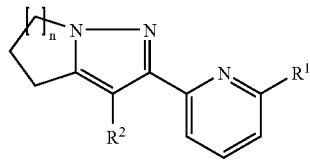

Formula I wherein
n is 1-2;
R$^1$ is hydrogen or C$_1$-C$_4$ alkyl;
R$^2$ is selected from the group consisting of 1-H-pyrrolo[2,3-b]pyridine, 1-H-pyrrolo[2,3-c]pyridine, 1-H-pyrazolo[3,4-b]pyridine, and 7-H-pyrrolo[2,3-d]pyrimidine all of which may be optionally substituted with C$_1$-C$_4$ alkyl or phenyl;
and the pharmaceutically acceptable salts thereof.

2. The compound of claim 1 wherein
n is 1;
R$^1$ hydrogen or methyl; and
R$^2$ is selected from the group consisting of unsubstituted 1-H-pyrazolo[3,4-b]pyridine and 7-H-pyrrolo[2,3-d]pyrimidine.

3. The compound of claim 1 wherein
n is 1;
R$^1$ hydrogen; and
R$^2$ is selected from the group consisting of unsubstituted 1-H-pyrrolo[2,3-b]pyridine and 1-H-pyrrolo[2,3-c]pyridine.

4. A pharmaceutical composition comprising a compound of claim 1 and a pharmaceutically acceptable carrier, excipient, or diluent.

* * * * *